United States Patent [19]

Leopold et al.

[11] Patent Number: 5,635,385
[45] Date of Patent: Jun. 3, 1997

[54] MULTI-UNIT RIBOZYME INHIBITION OF ONCOGENE GENE EXPRESSION

[75] Inventors: Lance H. Leopold, Philadelphia; Scott K. Shore, Ardmore; Moole V. R. Reddy, Upper Darby; E. Premkumar Reddy, Villanova, all of Pa.

[73] Assignee: Temple University-of the Commonwealth System of Higher Education, Philadelphia, Pa.

[21] Appl. No.: 122,795

[22] Filed: Sep. 15, 1993

[51] Int. Cl.$^6$ ............................. C12N 5/08; C12N 5/16; C12N 15/85; C07H 21/02
[52] U.S. Cl. ............................. 435/325; 435/6; 435/91.1; 435/91.3; 435/91.31; 435/172.3; 435/320.1; 435/372; 536/24.5; 536/25.1; 536/25.3; 514/44; 424/450
[58] Field of Search ............................. 514/44; 435/91.1, 435/91.21, 91.31, 91.32, 172.3, 320.1, 240.2, 6; 536/24.5, 25.1, 25.3; 424/450; 935/3, 5, 8, 10, 24, 34, 53–57

[56] References Cited

U.S. PATENT DOCUMENTS

| 5,087,617 | 2/1992 | Smith | 514/44 |
| 5,108,921 | 4/1992 | Low et al. | 435/240.1 |

FOREIGN PATENT DOCUMENTS

| WO91/04753 | 4/1991 | WIPO | A61K 47/48 |
| WO92/00080 | 1/1992 | WIPO | A61K 31/70 |
| WO92/22303 | 12/1992 | WIPO | A61K 31/70 |
| WO93/03141 | 2/1993 | WIPO | C12N 5/08 |

OTHER PUBLICATIONS

M. Cotten, TIBTECH, vol. 8 (Jul. 1990) pp. 174–178.
J. Rossi et al., Pharmac. Ther., vol. 50, pp. 245–254 ('91).
R. Stull et al., Pharmac. Res., vol. 12(4) ('95) pp. 465–479.
A. Coghlan, New Scientist (25 Nov. '95) 14–15.
D. Brown, Washington Post, 8 Dec. '95, pp. A1 & A22.
Bennett et al., Molecular Pharmacology, vol. 41, (1992), pp. 1023–1033.
Lemaitre et al., Proceedings of the National Academy of Sciences USA, vol. 84 (1987) pp. 648–652.
Mercola et al., Biochemical and Biophysical Research Communications, vol. 147, No. 1, (1987) pp. 288–294.
Miller, Blood, vol. 76, No. 2, (1990), pp. 271–278.
Snyder et al., "Ribozyme–Mediated Inhibition of bcr–abl Gene Expression in a Philadelphia Chromosome Positive Cell", Blood vol. 82, No. 2 (Jul. 15, 1993) pp. 600–605.
Wagner et al., "Transferrin–polycation Conjugates as Carrier for DNA Uptake into Cells" Proc. Natl. Acad. Sci. USA 87, 3410–3414 (1990).
B. Tseng et al. Cancer Gene Therapy, vol. 1, #1 (Mar. 1994) pp. 65–71.
M. Barinaga Science, vol. 262 (3 Dec. '94) pp. 1512–1514.
R. Weiss Science News, vol. 139 (16 Feb. '91) pp. 108–109.
R. Mulligan Science, vol. 260 (14 May '93) pp. 926–932.
C.–J. Chen et al. Nucleic Acids Research, vol. 20 (11 Sep. '92) pp. 4581–4589.
E. Shtivelman et al. Nature, vol. 315 (13 Jun. '85) pp. 550–554.
C. Szczylik, Science, vol. 253 (2 Aug. '91) pp. 562–565.
A. Gutierrez et al. The Lancet, vol. 339 (21 Mar. '92) pp. 715–721.
W. James Antiviral Chemistry & Chemotherapy, vol. 2 #4 ('91) pp. 191–214.
M. Lemaitre et al. PNAS, vol. 84 (Feb. 1987) pp. 648–652.

Primary Examiner—Charles C. P. Rories
Attorney, Agent, or Firm—Seidel, Gonda, Lavorgna & Monaco, P.C.

[57] ABSTRACT

A novel multi-unit ribozyme is provided which is capable of selectively cleaving the mRNA transcript of a hybrid oncogene resulting from a chromosomal translocation. Specialized delivery vehicles such as liposomes, and growth factor conjugates for cellular uptake by receptor-mediated endocytosis, are also described. The multi-unit ribozyme is used for the treatment of neoplasms characterized by expression of the oncogene. In one embodiment, a multi-unit ribozyme is provided which cleaves the mRNA transcript of Philadelphia chromosome-positive cells, thereby blocking production of the tumorigenic p210$^{bcr-abl}$ fusion protein.

21 Claims, 5 Drawing Sheets

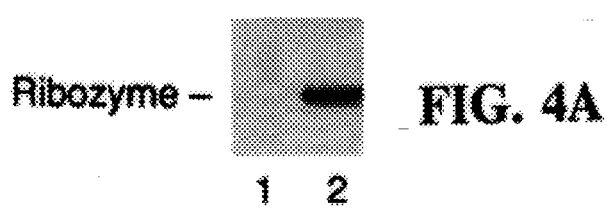
FIG. 4A
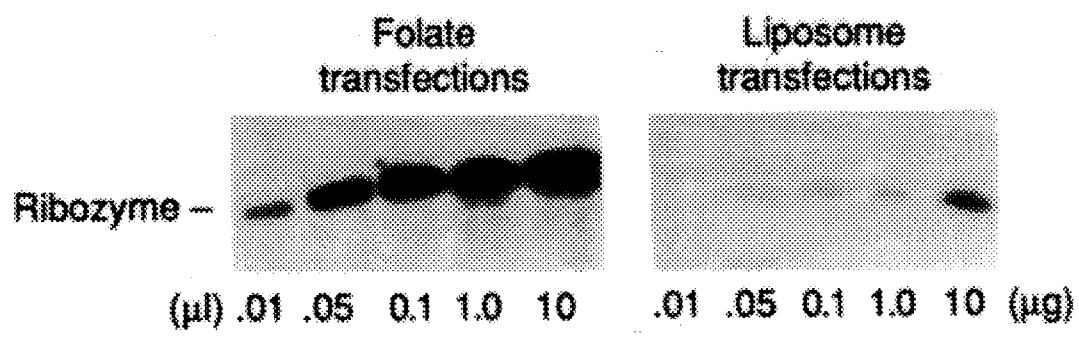
FIG. 4B  FIG. 4C

MULTI-UNIT RIBOZYME INHIBITION OF ONCOGENE GENE EXPRESSION

Reference to Government Grant

The invention described herein was supported in part by National Institutes of Health grants P01 CA 52009 and 47937. The government has certain rights in the invention.

FIELD OF THE INVENTION

The invention relates to the inhibition of oncogene expression by ribozymes complementary to oncogene mRNA transcripts. The invention further relates to the therapeutic use of such ribozymes in the treatment of neoplastic diseases. In one embodiment, the invention relates to the treatment of leukemias characterized by the Philadelphia chromosome translocation.

BACKGROUND OF THE INVENTION

Chronic myelogenous leukemia (CML) accounts for 20% of all cases of leukemia and carries a death rate of 1.5 per 100,000 population (Lichtman, *chronic Myelogenous Leukemia and Related Disorders in Hematology*, Williams (ed.) 4th Ed., McGraw Hill, New York, N.Y. (1990)). In 1960, Nowell and Hungerford discovered that the Philadelphia chromosome (Ph+) was consistently associated with CML (reviewed in Rosson and Reddy, *Mutation Res.*, 195, 231–243 (1988)). Molecular studies have demonstrated that during the formation of the Philadelphia chromosome, a portion of the c-abl gene is translocated from chromosome 9q34 to chromosome 22q11, resulting in the formation of a chimeric gene consisting of sequences derived from the BCR and ABL loci (Heisterkamp et al., *Nature*, 306, 239 (1983); Heisterkamp et al., *Nature*, 315, 758 (1985)). This translocation is detectable in over 95% of patients with CML. A significant portion of acute lymphocytic leukemia (ALL) patients also carry the $Ph^1$ chromosome.

The fusion gene, named bcr-abl, transcribes a chimeric mRNA of 8.5 kb which is translated to a $p210^{bcr-abl}$ fusion protein with altered tyrosine kinase activity (Konopka and Witte, *Mol. Cell Biol.*, 5, 3116–3123 (1985); Kurzrock et al., *N. Engl. J. Med.*, 319, 990 (1988)). The $p210^{bcr-abl}$ protein has been shown to transform myeloid precursor cells in vitro (McLaughlin et al., *Proc. Natl. Acad. Sci. USA*, 84, 8558 (1987)). In addition, infecting murine bone marrow stem cells with a retrovirus containing the bcr-abl gene produces a disorder similar to human CML in mice (Daley et al., *Science*, 247, 824 (1990); Voncken et al., *Blood*, 79, 1029–1036 (1992))

It has been shown using antisense molecules that interrupting the bcr-abl transforming signal can inhibit the cell growth of isolated blast cells from CML patients (Szczylik et al., *Science*, 253, 562 (1991); WO 92/22303 (1992)).

In the past decade, the use of antisense nucleic acid sequences to block the function of a mRNA has been developed as a strategy to inhibit viral and malignant diseases (Weintraub, *Sci. Amer.* 262, 34–40 (1990)). More recently, it has been shown that specific RNA sequences have catalytic activity (Kruger et al., *Cell* 81, 147–157 (1982)). These molecules are termed "ribozymes". Several different catalytic sequences have been described with a common need for divalent cations, which cause nonhydrolytic transesterification of specific RNA target regions (Symons, *Annu. Rev. Biochem.* 61, 641–671 (1992)). These catalytic sequences have been modified to create antisense molecules which bind to and cleave specific target RNA molecules (Zaug et al., *Nature*, 324, 4229–4233 (1986); Uhlenbeck, *Nature* 328, 596–600 (1987)).

Snyder et al., *Blood* 82,600–605 (1993) have shown that liposome vectors containing a single-unit DNA-RNA hybrid ribozyme can inhibit cr-abl gene expression and cell growth in a Ph-positive cell line. Other reports of ribozyme-mediated inhibition of cr-abl gene expression include WO 93/03141 (1993), and WO 92/00080 (1992) and the corresponding Reddy et al., U.S. Pat. No. 5,246,921. The "hammerhead" ribozyme has been developed into a targeted ribozyme, employing a catalytic "hammerhead" domain and flanking oligonucleotides that specifically bind to target sequences (Walbot, *Nature* 334, 585–591 (1988)). Cleavage occurs 3' to a GUX triplet where X can be C, U, or A (Guerrier-Takada et al., *Cell* 35, 848–852 (1983); Cech & Bass, *Annu. Rev. Biochem.* 55, 599–629 (1986); Symons, *Trends Biochem Sci.* 14, 445–50 (1989)). Any GUX sequence can be targeted by the appropriate design of the flanking oligonucleotide sequence.

There are no conventional therapies including chemotherapy, $^{32}P$-treatment and splenic irradiation, that have resulted in cures in CML (Lichtman, *Chronic Myelogenous Leukemia and Related Disorders in Hematology*, W. J. Williams, Ed., 4th Edition, McGraw Hill, New York, N.Y. (1990)). Five to 15% of patients receiving alpha-interferon therapy may suppress the expression of the Ph-positive clone in CML (Talpaz et al., *N. Engl. J. Med.* 314, 1865–1859 (1986). However, the ability of interferon to cure CML is not proven. Allogeneic bone marrow transplant (BMT), using HLA identical siblings, following myeloablative chemo-radiotherapy is curative in up to 85% of carefully selected patients in chronic phase CML (Goldman et al., *N. Engl. J. Med.* 314, 202–207 (1986); Thomas et al., *Amer. Intern.* Med.104, 155–166 (1986); Marks et al., *Br. J. Haematol.* 81, 383–390 (1992)). In CML patients transplanted with an identical twin following high dose myeloablative therapy, the cure rate is 50%. This difference is due to a graft-versus-leukemia (GVL) effect and is enhanced by the presence of chronic graft versus host disease (GVHD). T-cell depletion of donor marrow reduces the GVL effect, the incidence of GVHD, as well as the cure rate (Gale et al., *Bone Marrow Transplantation* 9, 83–85 (1992)). Collectively, these data show that high dose therapy given early in the course of CML is potentially curative in 50% of patients. The additional curative effects of allogeneic BMT are due to a GVL effect.

Unfortunately, less than 30% of CML patients will have a normal allogeneic HLA matched donor. Current use of matched unrelated donors has resulted in high mortality due to GVHD and infections (Marks et al., *Ann. Int. Med.* 119, 207–214 (1993)). Thus, the development of an autologous marrow transplant program using Ph-negative stem cells, would provide an alternative for patients without other curative options. An autologous BMT would avoid GVHD and should be curative in up to 50% of patients, provided the marrow is purged free of CML stem cells. In preparation for autologous marrow infusion, marrow cells are harvested from the affected individual, are "purged" of leukemia cells by chemical agents, and returned to the patient following extensive chemotherapy or total body radiation.

Thus far, autologous BMT has not been successful in CML because Ph-positive stem cells are invariably reinfused into the patient (Reiffers et al., *British aematology* 77, 339–345 (1991)). In an attempt to provide Ph-negative stem cells for autologous BMT, chemotherapeutic purging (Silvestri et al., *Int. J. Cell Cloning* 9, 474–490 (1990)), interferon purging (McGlave et al., *Bone Marrow Trans-*

*plantation* 6, 115–120 (1990)), long term bone marrow cultures (Barnett et al., *Bone Marrow Transplantation* 4, 345–351 (1989)), and CD34 stem cell selection (Verfaillie et al., *Blood* 79, 1008–1010 (1992)) have all been attempted and may result in transient Ph-negative hematopoiesis. Using antisense molecules, Szczylik et al., *Science*, 253, 562 (1991) and WO 92/22303 (1992) inhibited the cell growth of isolated blasts from CML patients.

While the presently known bcr-abl ribozymes (Snyder et al., *Blood* 82, 600–605 (1993) and WO 93/03141 (1993); Reddy et al., WO 92/00080 and U.S. Pat. No. 5,246,921) are promising, there is a need for bcr-abl ribozymes with increased catalytic potential for oncogenic bcr-ablmRNA, without causing substantial cleavage of normal c-abl and bcr transcripts. There is also a need for bcr-abl ribozyme vectors having improved uptake.

SUMMARY OF THE INVENTION

A synthetic RNA molecule useful for the treatment of a neoplasm characterized by the presence of a hybrid oncogene resulting from a chromosomal translocation is provided comprising (a) a first ribozyme subunit comprising
  (i) a first flanking segment having a nucleotide sequence complementary to the nucleotide sequence of a portion of the oncogene mRNA transcript substantially 5' of the oncogene translocation junction and being hybridizable to that mRNA portion;
  (ii) a second flanking segment having a nucleotide sequence complementary to the nucleotide sequence of a portion of the oncogene mRNA transcript substantially 3' of the bcr-abl translocation junction and being hybridizable to that mRNA portion;
  (iii) a catalytically active segment disposed between the first and second flanking segments comprising a ribozyme capable of cleaving the oncogene mRNA at or near the translocation junction; and (b) two or more additional ribozyme subunits, each subunit comprising a catalytically active segment comprising a ribozyme capable of cleaving the oncogene mRNA and flanking segments complementary to the bcr-abl mRNA transcript and hybridizable thereto.

According to one embodiment of the invention, a synthetic RNA molecule is provided for the treatment of leukemia. For example, where the oncogene is bcr-abl, a synthetic RNA molecule targeting the bcr-abl mRNA is provided, which may be used for the treatment of Ph-positive leukemias.

According to another embodiment, a recombinant vector is provided comprising DNA which when expressed will provide such a synthetic RNA molecule.

In yet another embodiment, the invention is a pharmaceutical composition comprising the aforesaid synthetic RNA molecule and a pharmaceutically acceptable carrier. The carrier may comprise, for example, a liposome.

In a further embodiment, the invention takes the form of a conjugate comprising the synthetic RNA molecule linked to a cell surface ligand-binding molecule, for improved cellular uptake.

A therapeutic method for the treatment of a patient afflicted with a neoplasm characterized by the presence of a hybrid oncogene resulting from a chromosomal translocation is provided. The method comprises contacting cells of the patient with an effective amount of the synthetic RNA molecule for a time sufficient to cleave the oncogene mRNA and inhibit the expression of that gene. The method may be carried out in vivo or in vitro. According to an in vitro method comprising a bone marrow purging procedure, bone marrow cells aspirated from a leukemia patient, e.g., a Ph-positive leukemia patient, are treated with a synthetic RNA molecule of the invention to purge leukemic cells. The purged marrow cells are then returned to the body of the afflicted individual.

The proliferation of cells characterized by the presence of a hybrid oncogene resulting from a chromosomal translocation may be inhibited by introducing into such cells an artificially-constructed gene which, upon transcription in said cell, produces the synthetic RNA molecule of the invention, which cleaves the oncogene mRNA and thereby inhibits proliferation of the cells. The artificially-constructed gene may be introduced into the susceptible cells by, for example, transfection, by a transducing viral vector or by microinjection.

DESCRIPTION OF THE FIGURES

FIG. 3A, lane S shows the cleavage of c-abl control mRNA (no ribozymes), in comparison to cleavage with ribozymes D and G. FIG. 3B shows the cleavage of bcr control mRNA (no ribozymes), in comparison to cleavage with ribozymes B and G.

FIGS. 4A, 4B and 4C comprise autoradiograms of transfection by a triple-unit ribozyme with different delivery vehicles. FIG. 4A compares K562 cell transfection with naked ribozyme (lane 1) versus transfection with ribozyme in liposome vector. FIG. 4B and 4C compare 32D cell transfection using 1 μg of ribozyme with increasing quantities of folate-polylysine (FIG. 4B) or lipofectin (FIG. 4C) as a vehicle.

DETAILED DESCRIPTION OF THE INVENTION

The invention provides a synthetic RNA molecule which acts as a multi-unit ribozyme. The multi-unit ribozyme more efficiently cleaves target oncogene mRNA than single unit ribozymes alone or in combinations. The inventive ribozyme is specific for the hybrid oncogene, since it only poorly cleaves mRNA transcripts of the parent proto-oncogenes whose translocation results in the hybrid oncogene. Thus, only cells containing the chromosomal translocation resulting in the expression of the oncogene are affected.

Without limiting the generality of the foregoing, the invention in one preferred embodiment comprises such multi-unit ribozymes which target hybrid oncogenes characteristic of leukemias. Such disorders include, for example, CML and acute lymphocytic leukemia, and other leukemias, such as those involving the c-myc proto-oncogene and cl-1 and bcl-2. These disorders are characterized by the presence of a tumorigenic chimeric protein resulting from a chromosomal translocation. The multi-unit ribozyme of the invention is designed to cleave the mRNA encoding the tumoregenic protein at a site on the mRNA at or near the translocation junction.

Furthermore, without limiting the generality of the foregoing, the invention is exemplified by a novel RNA molecule designed for cleavage of the bcr-abl mRNA, which mRNA translates the p210 $^{bcr-abl}$ protein characteristic of Ph-positive leukemias. However, as noted above, the present invention is not limited to this molecule, but encompasses other molecules designed according to the invention for cleavage of similar genes in other cancers. Ribozymes according to the invention include catalytically active segments for cleaving the selected target chimeric gene transcript after the ribonucleotide sequence G-U-X, wherein X is the ribonucleotide A, U or C.

Figure 1:
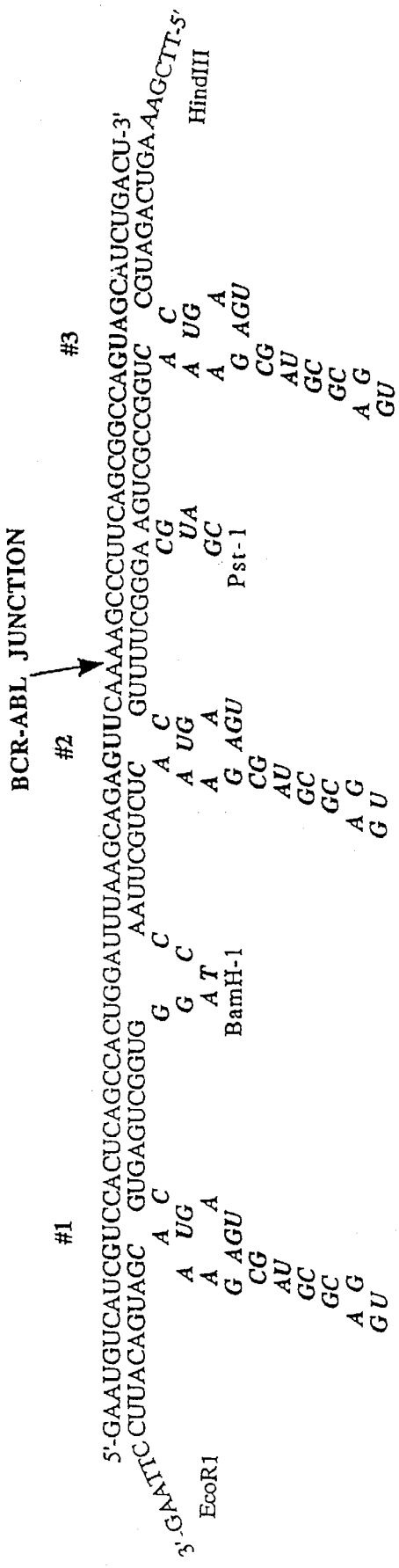
FIG. 1 is a schematic of a triple-unit ribozyme according to the invention (SEQ ID NO:1), shown in hybridizing relationship with the translocation junction portion of the target complementary bcr-abl mRNA transcript. Restriction sites for assisting in the cloning of the molecule, or in the cloning of subunits thereof, are indicated. The translocation junction is also indicated.

While the presently preferred ribozyme, as exemplified by FIG. 1, contains three sub-units, ribozymes of four, five, six, seven, eight or more subunits are contemplated. The multi-unit ribozyme targets the oncogene mRNA transcript. Each ribozyme subunit contains a catalytically active segment comprising a ribozyme capable of cleaving oncogene mRNA and flanking segments having a nucleotide sequence complementary to portions of the oncogene mRNA. The flanking sequences serve as "annealing arms" providing specificity of the ribozyme for the oncogene transcript.

It should be noted that absolute complementarity of the annealing arms to the target oncogene mRNA transcript is not necessary. For instance, the multi-unit ribozyme may include restriction enzyme cleavage sites separating the subunits, to aid in cloning of the intact multiple-unit ribozyme or its separate subunits. Thus, reference herein to an oligonucleotide segment "having a nucleotide sequence complementary to the nucleotide sequence of a portion of an oncogene mRNA transcript" does not necessarily mean a sequence having 100% complementarity with the transcript. In general, the multi-unit ribozyme as a whole will have sufficient complementarity to the target message to form a duplex therewith of sufficient stability to allow the catalytically active segments of the ribozyme to cleave the message at the target GUX sites. Thus, only sufficient complementarity to permit the ribozyme to be "hybridizable" with the target message is required. One skilled in the art may readily determine the degree of mismatching which may be tolerated, based upon the melting point, and therefore the stability, of the duplex.

The annealing arms may comprise segments of any length effective in imparting the necessary degree of target specificity to the ribozyme. Preferably, each annealing arm comprises from about 4 to about 24 nucleotides, most preferably from about 6 to about 12 nucleotides.

The triple-unit ribozyme exemplified by FIG. 1 contains three catalytic segments which are positioned so as to cleave the target bcr-abl mRNA at a GUC triplet 32 nucleotides upstream (i.e., in the 5'-direction) from the cr-bl junction, in the bcr-derived portion of the transcript; at a GUU triplet 4 nucleotides upstream from the junction; and at a GUA triplet in the abl-derived portion of the transcript, located 17 nucleotides downstream (i.e., in the 3'-direction) from the bcr-abl junction. The complete cDNA encoding the p210$^{bcr-abl}$ protein is disclosed by Schtivelman et al., Nature 315, 550–553 (1985), the entire disclosure of which is incorporated herein by reference. As the cDNA sequence indicates, there are yet additional GUX cleavage sites, disposed even further from the translocation junction, which may be targeted by a larger multi-unit ribozyme according to the present invention.

Preferably, at least one, and more preferably all, the catalytic segments comprise the ribonucleotide sequence CUGAUGAGUC CGUGAGGACG AAA (SEQ ID NO:8). Cleavage of the target RNA occurs after the GUX sequence wherein X is A, U or C, generating 2'-3' cyclic phosphate and 5'-hydroxyl. After the target is cleaved, the multi-unit ribozyme is designed to release the cleaved substrate fragments. The ability to release the fragments is to some extent dependent on the length of the flanking sequences. The same multi-unit ribozyme may then cleave other messages and release the fragments until the molecule is degraded.

The ribozyme of the invention may be prepared by chemical synthesis or produced in recombinant vectors by conventional means. See, Molecular Cloning: A Laboratory Manual, Cold Spring Harbor Laboratory (2nd ed., 1989). The ribozyme RNA sequences may be synthesized conventionally, for example, by using RNA polymerases such as T7 or SP6. According to one method exemplified in the examples below, cDNA encoding the single-unit 23-mer ribozyme SEQ ID NO:1 is synthesized, ligated into multi-unit ribozyme cDNA and cloned into conventional commercially-available vectors such as PGEM3z, by conventional techniques. Ribozyme RNA is then transcribed with an RNA polymerase, e.g., T7 or SP6, by conventional protocols. The protocols of the commercial suppliers of the cloning vectors and RNA polymerase may be conveniently followed.

Alternatively, synthetic double-stranded oligodeoxyribonucleotide with flanking restriction sites 5 (e.g., BamHI sites) may be prepared and used to carry out in vitro polymerization (PCR) utilizing Taq polymerase, as described in WO 93/03141 (1993), incorporated herein by reference. The PCR product is then cloned into the corresponding restriction site (e.g., BamHI) of a conventional vector, e.g. pBLUESCRIPT II KS vector (Stratagene, La Jolla, Calif.). Transcription of RNA from the plasmid vector using T7 promotor is carried out, as described in WO 93/03141.

For therapeutic use, the multi-unit ribozyme may be combined with a pharmaceutical carrier, such as a suitable liquid vehicle or excipient and an optional auxiliary additive or additives. The liquid vehicles and excipient are conventional and commercially available. Illustrative thereof are distilled water, physiological saline, aqueous solution of dextrose, and the like. For in vivo use the ribozyme is preferably administered parenterally, most preferably intravenously. The vehicle is designed accordingly. Alternatively, the agent be administered subcutaneously via controlled release dosage forms.

In addition to administration with conventional carriers, the ribozyme may be administered by a variety of specialized oligonucleotide delivery techniques. For example, the ribozyme may be encapsulated in liposomes for therapeutic delivery, according to conventional oligonucleotide encapsulation techniques. The oligonucleotide, depending upon its solubility, may be present both in the aqueous layer and in the lipidic layer, or in what is generally termed a liposomic suspension. The hydrophobic layer, generally but not exclusively, comprises phospholipids such as lecithin and sphingomyelin, steroids such as cholesterol, ionic surfactants such as diacetylphosphate, stearylamine, or phosphatidic acid, and/or other materials of a hydrophobic nature. Oligonucleotides have been successfully encapsulated in unilamellar liposomes. The liposome interacts spontaneously with DNA or RNA to form a lipid-DNA or lipid-RNA complex with complete entrapment of the DNA or RNA, and the fusion of this complex with cell membranes results in efficient uptake of DNA or RNA. Liposomes formed from cationic materials, e.g., N-[1-(2,3-dioleyloxy)propyl]-N,N,N-trimethylammonium chloride (DOTMA), are preferred.

Reconstituted Sendai virus envelopes have been successfully used to deliver RNA and DNA to cells. Arad et al., *Biochem. Biophy. Acta.* 859, 88–94 (1986).

The ribozyme may be conjugated to poly(L-lysine) to increase cell penetration. Such conjugates are described by Lemaitre et al., *Proc. Natl. Acad. Sci. USA*, 84, 648–652 (1987). The resulting aldehyde groups are then randomly coupled to the ε-amino groups of lysine residues of poly(L-lysine) by Schiff base formation, and then reduced with sodium cyanoborohydride. This procedure converts the 3'-terminal ribose ring into a morpholine structure.

The ribozyme may be conjugated for therapeutic administration to cell surface ligand-binding molecules which recognize cell-surface molecules, such as according to WO 91/04753 (1991), the entire disclosure of which is incorporated herein by reference. The ligand-binding molecule may comprise, for example, an antibody against a cell surface antigen, an antibody against a cell surface receptor, a growth factor having a corresponding cell surface receptor, an antibody to such a growth factor, or an antibody which recognizes a complex of a growth factor and its receptor. Methods for conjugating ligand-binding molecules to oligonucleotides are detailed in WO 91/04753.

In particular the growth factor may comprise transferrin or folate. Transferrin-polylysine-oligonucleotide complexes or folate-polylysine-oligonucleotide complexes may be prepared for uptake by cells expressing high levels of transferrin or folate receptor. The preparation of transferrin complexes as carriers of oligonucleotide uptake into cells is described by Wagner et al., *Proc. Natl. Acad. Sci. USA* 87, 3410–3414 (1990). The preparation of folate complexes is described in the examples, below. Inhibition of leukemia cell proliferation by transferrin receptor-mediated uptake of c-myb antisense oligonucleotides conjugated to transferrin has been demonstrated by Citro et al., *Proc. Natl. Acad. Sci. USA* 89, 7031–7035 (1992). Cellular delivery of folate-macromolecule conjugates via folate receptor endocytosis, including delivery of an antisense oligonucleotide, is described by Low et al., U.S. Pat. No. 5,108,921. Also see, Leamon et al., *Proc. Natl. Acad. Sci. USA* 88, 5572 (1991).

As an alternative to treatment with exogenous ribozyme, the therapeutic agent may be synthesized in situ in the targeted neoplastic cells with a vector containing an artificially-constructed gene comprising a transcriptional promotor and DNA encoding the ribozyme. Upon transcription, the gene segment transcribes the ribozyme in situ in the targeted cell. The endogenously produced RNA hybridizes to the relevant mRNA, resulting in interference with the target gene's function and inhibition of the proliferation of the targeted neoplastic cell.

The promotor segment of the artificially-constructed gene serves as a signal-conferring expression of the inserted DNA which lies downstream thereof. It will include all of the signals necessary for initiating transcription of the sequence. The promotor may be of any origin as long as it specifies a rate of transcription which will produce sufficient quantities of the ribozyme to inhibit the expression of the target oncogene, and therefore the proliferation of the tumorigenic cells expressing that gene. Preferably, a highly efficient promotor such as a viral promotor is employed. Other sources of potent promotors include cellular genes that are expressed at high levels. The promotor segment may comprise a constitutive or a regulatable promotor. A typical construct will utilize the SV40 promotor or Maloney murine leukemia virus long terminal repeat (LTR) sequences.

The artificial gene may be introduced by any of the methods described in U.S. Pat. No. 4,740,463, incorporated herein by reference. One technique is transfection, which can be performed by several different methods. One method of transfection involves the addition of DEAE-dextran to increase the uptake of the naked DNA molecules by a recipient cell. See McCutchin, J. H. and Pagano, J. S., *J. Natl. Cancer Inst.* 41, 351–7 (1968). Another method of transfection is the calcium phosphate precipitation technique which depends upon the addition of $Ca^{++}$ to a phosphate-containing DNA solution. The resulting precipitate apparently includes DNA in association with calcium phosphate crystals. These crystals settle onto a cell monolayer; the resulting apposition of crystals and cell surface appears to lead to uptake of the DNA. A small proportion of the DNA taken up becomes expressed in a transfectant, as well as in its clonal descendants. ee Graham, F. L. and van der Eb, A. J., *Virology* 52, 456–467 (1973) and *Virology* 54, 536–539 (1973). Transfection may also be carried out by cationic phospholipid-mediated delivery. In particular, polycationic liposomes can be formed from N-[1-(2,3-dioleyloxy)propyl]-N,N,N-trimethylammonium chloride (DOTMA). See Felgner et al., *Proc. Natl. Acad. Sci. USA* 84, 7413–7417 (1987) (DNA-transfection); Malone et al., *Proc. Natl. Acad. Sci. USA*, 86, 6077–6081 (1989) (RNA-transfection); Zhu et al., *Science* 261, 209–211 (1993). Polylysine-folate mediated transfection, as described elsewhere herein, may also be used.

Alternatively, the artificially-constructed gene can be introduced in to cells, in vitro or in vivo, via a transducing viral vector. See Tabin et al., *Mol. cel. Biol.* 2,426–436 (1982). Use of a retrovirus, for example, will infect a variety of cells and cause the artificial gene to be inserted into the genome of infected cells. Such infection could either be performed with the aid of a helper retrovirus, which would allow the virus to spread through the organism, or the antisense retrovirus could be produced in a helper-free system, such as ψ2-like cells (See Mann et al., *Cell* 33, 153–160, 1983) that package amphotropic viruses. A helper-free virus might be employed to minimize spread throughout the organism. Viral vectors in addition to retroviruses can also be employed, such as papovaviruses, SV40-like viruses, or papilloma viruses. The use of retroviruses for gene transfer has been reviewed by Eglitis and Anderson, *BioTechniques* 6, 608–614 (1988).

According to one embodiment of retroviral delivery, the multi-unit ribozyme sequence is cloned into a vector containing a transcriptionally active CMV promotor, an SV-40 viral promotor, the human β-actin gene promotor, and the T7 polymerase promotor. The constructs may contain a marker, e.g., the gene for neomycin resistance, to allow for selection of useful clones. These DNA constructs are transfected into PA317 fibroblast cells by the calcium-phosphate precipitation method. Cells are plated and grown in the presence of neomycin to select for clones containing DNA coding for ribozymes. These clones are screened for ribozyme RNA using the RNAzol isolation procedure followed by RT-PCR analysis with primers that amplify the ribozyme sequence. NIH-3T3 cells are infected by serial dilution of virus containing supernatant from the PA317 clones in order to determine the most efficient ribozyme producing clones. These are selected for infection of oncogene-expressing cells. Infected cells may be assayed for the chromosomal translocation by detection of the relevant mRNA transcript using RTPCR analysis, or by detection of the tumorgenic protein by immunoprecipitation. It may be appreciated that in the case of retroviral delivery of a multi-unti ribozyme specific for bcr-abl, infected cells are assayed for the bcr-abl translocation by detection of the bcr-abl mRNA transcript or by detecting the p210 $^{bcr-abl}$ protein.

Presently preferred vectors are retroviral vectors, adenoviral vectors, vaccinia vectors, and others, such as described by E. Gilboa, *Adv. Exp. Med. Biol.*, 241:29 (1988) and P. H. Pouwels et al., "Vectors for Animal Cells", in *Cloning Vectors: A Laboratory Manual*, ch. 7 (Elsevier, Amsterdam: 1985). Other conventionally employed vectors designed for use in mammalian, bacterial, yeast, fungal or insect systems may be employed to recombinantly express the ribozyme of this invention, as exemplified by FIG. 1, but are not preferred for delivery purposes into the cells.

Vesicle fusion could also be employed to deliver the artificial gene. Vesicle fusion may be physically targeted to the tumor tissue if the vesicle were appropriately designed to be taken up by the cells containing the target gene. Such a delivery system would be expected to have a lower efficiency of integration and expression of the artificial gene delivered, but would have a higher specificity than a retroviral vector. A combination strategy of targeted vesicles containing papilloma virus or retrovirus DNA molecules might provide a method for increasing the efficiency of expression of targeted molecules.

Still another alternative is to introduce the artificial gene via micro-injection. See for example, Laski et al., *Cell*, 1982.

Particulate systems and polymers for in vitro and in vivo delivery of polynucleotides was extensively reviewed by Felgner in *Advanced Drug Delivery Reviews* 5, 163–187 (1990). Techniques for direct delivery of purified genes in vivo, without the use of retroviruses, has been reviewed by Felgner in *Nature* 349, 351–352 (1991). Such methods of direct delivery of polynucleotides may be utilized for local delivery of either exogenous ribozyme or artificially-constructed genes producing the ribozyme in situ.

Recently, Wolf et al. demonstrated that direct injection of non-replicating gene sequences in a non-viral vehicle is possible. ee *Science*, 247, 1465–1468 (1990). DNA injected directly into mouse muscle did not integrate into the host genome, and plasmid essentially identical to the starting material was recovered from the muscle months after injection. Interestingly, no special delivery system is required. Simple saline or sucrose solutions are sufficient to delivery DNA and RNA.

Preferably, treatment of leukemias, including treatment of Ph-positive leukemias, is accomplished by contacting bone marrow cells extracted from a patient ex vivo with a sufficient number of ribozymes, or vectors carrying ribozymes, for a time sufficient to effect cleavage of the oncogene present in the cells. Alternatively, the method may employ contacting the cells in vivo, for example, by administration directly into the bone marrow of a leukemic patient of vectors carrying the RNA molecule of the invention. When either method is applied to the cells of CML patients, the RNA molecule of the invention, as exemplified by FIG. 1, causes the specific destruction of the bcr-abl mRNA, resulting in the loss of synthesis of the tumorigenic p210 $^{bcr-abl}$ protein.

Once transmitted into the cellular environment via a vector, the ribozyme is expected to survive within the cell for a short period of time. Since the relationship between the ribozyme and the target oncogene is not necessarily one-to-one, a single ribozyme is expected to bind and cleave a number of oncogenic transcripts before being degraded or destroyed by the natural enzymes in the cells and/or the natural functions of the immune system.

High dose chemotherapy coupled with autologous bone marrow rescue involves removing a portion of the patient's bone marrow, treating the patient with conventional chemotherapy or radiation to substantially destroy the remaining bone marrow cells carrying the hybrid oncogene, treating the stored bone marrow with a ribozyme specific for the mRNA transcript of the oncogene, and returning the treated cells to the patient. The treated cells, when returned to the patient, may be stimulated by various known hematopoietic growth factors to repopulate the bone marrow with cells which do not carry the oncogenic transcript.

According to a method for bone marrow purging, bone marrow is harvested from a donor by standard operating room procedures from the iliac bones of the donor. Methods of aspirating bone marrow from donors are well-known in the art. Examples of apparatus and processes for aspirating bone marrow from donors are disclosed in U.S. Pat. Nos. 4,481,946 and 4,486,188, incorporated herein by reference. Sufficient marrow is withdrawn so that the recipient, who is either the donor (autologous transplant) or another individual (allogeneic transplant), may receive from about 4 ×10$^8$ to about 8 ×10$^8$ processed marrow cells per kg of body-weight. This generally requires aspiration of about 750 to about 1000 ml of marrow. The aspirated marrow is filtered until a single cell suspension, known to those skilled in the art as a "buffy coat" preparation, is obtained. This suspension of leukocytes is treated with ribozyme in a suitable carrier, advantageously in a concentration of about 50–100 μg/ml. Alternatively, the leucocyte suspension may be stored in liquid nitrogen using standard procedures known to those skilled in the art until purging is carried out. The purged marrow can be stored frozen in liquid nitrogen until ready for use. Methods of freezing bone marrow and biological substances are disclosed, for example, in U.S. Pat. Nos. 4,107,937 and 4,117,881.

Other methods of preparing bone marrow for treatment with ribozymes may be utilized, which methods may result in even more purified preparations of hematopoietic cells than the aforesaid buffy coat preparation.

One or more hematopoietic growth factors may be added to the aspirated marrow or buffy coat preparation to stimulate growth of hematopoietic neoplasms, and thereby increase their sensitivity to the toxicity of the ribozyme. Such hematopoietic growth factors include, for example, IL-3 and granulocyte macrophage colony stimulating factor (GM-CSF). The recombinant human versions of such growth factors are advantageously employed. After treatment with the ribozyme, the cells to-be-transferred are washed with autologous plasma or buffer to remove unincorporated drug. The washed cells are then infused back into the patient. Other methods for bone marrow purging utilizing antisense oligonucleotide are disclosed in U.S. Pat. No. 5,087,617, incorporated herein by reference.

According to a preferred treatment regimen for bone marrow purging, the aspirated bone marrow is contacted daily or twice daily for approximately one to four days with an amount of ribozyme effective to overcome the malignant phenotype.

For in vivo administration, the amount of ribozyme may vary depending on the extent of the neoplasm, the particular ribozyme utilized, and other factors. The actual dosage administered may take into account the size and weight of the patient, whether the nature of the treatment is prophylactic or therapeutic in nature, the age, health and sex of the patient, the route of administration, whether the treatment is regional or systemic, and other factors.

Sufficient ribozyme should be administered to achieve an intracellular concentration of from about 1 to about 100 µg/ml. The patient should receive a sufficient daily dosage to achieve these concentrations of drug. The daily dosage may range from about 0.1 to 1,000 mg oligonucleotide per day, preferably from about 100 to about 700 mg per day. Greater or lesser amounts of the oligonucleotide may be administered, as required. Those skilled in the art should be readily able to derive appropriate dosages and schedules of administration to suit the specific circumstances and needs of the patient. It is contemplated that a course of treatment may advantageously comprise infusion of the recommended daily dose of ribozyme for a period of from about 3 to about 28 days, more preferably from about 7 to about 10 days. Those skilled in the art should readily be able to determine the optimal dosage in each case.

For other antisense oligonucleotide drugs, it has been found that a daily oligonucleotide dosage of 250–300 mg will provide an extracellular oligonucleotide concentration of 1.5–2.5 µM which, based upon in vitro studies, has been established as an effective concentration. Thus, for an about 70 kg adult human being, a daily dose of about 250–350 mg oligonucleotide is believed sufficient to achieve an effective extracellular concentration. For children, the daily dosage is reduced proportionately according to the weight of the patient.

The therapeutic end point for either in vivo or ex vivo treatment may be assessed by the absence of cells expressing the relevant chromosomal translocation (e.g., bcr-abl). Recent methods for detecting leukemic cells have focused on detecting the presence of the oncogene, or its corresponding mRNA, in cells of the bone marrow. See, for example, the following U.S. Patents, incorporated herein by reference: U.S. Pat. No. 4,681,840, 4,857,466 and 4,874,853. Also see Kawasaki et al., *Proc. atl. Acad. Sci. USA* 85, 5698–5702 (1988). The presence of even a few copies of the target oncogene can be effectively detected by amplification using reverse transcriptase polymerase chain reaction (RT-PCR) technology.

The practice of the invention is illustrated by the following non-limiting examples.

EXAMPLE 1

Synthesis of Multi-unit Ribozyme cDNA encoding the single-unit 23-mer ribozyme CUGAUGAGUC CGUGAGGACG AAA (SEQ ID NO:1 ) was synthesized. The single-unit ribozyme cDNA was ligated into double and triple unit ribozymes and cloned into PGEM3z vector (Promega, Madison, Wis.) (1 µl DNA, 1 µl 10X buffer, 7 µl water, 1 µl low-concentration T4 ligase at 1 U/µl, followed by incubation overnight at 15° C.). Ribozyme RNA was transcribed using SP6 RNA polymerase in vitro according to the manufacturer's (Promega) protocol (4 µl 5X TSC buffer; 100 nM DTT; 0.5 µL RNase inhibitor; 1 µg template DNA; 4 µl 11:1:1:1 mixture of NTPs—U, A, G and C; 1 µl 1 T7 or SP6 RNA polymerase; incubate at 37° C. for 1 hr, then purify product by cold ETOH precipitation). The various ribozymes targeting sites #1, #2 and/or #3 of the bcr-abl mRNA shown in FIG. 1 were as follows:

(A) SEQ ID NO:7—single-unit ribozyme targeting site #2
(B) SEQ ID NO:2—single-unit ribozyme targeting site #1
(C) SEQ ID NO:3—single-unit ribozyme targeting site #2
(D) SEQ ID NO:4—single-unit ribozyme targeting site #3
(E) SEQ ID NO:5—double-unit ribozyme targeting sites #1,2
(F) SEQ ID NO:6—double-unit ribozyme targeting sites #2,3
(G) SEQ ID NO:1—triple-unit ribozyme targeting sites #1,2,3

The two different two-subunit ribozymes targeting site #2 differed in the length of the annealing arms. Ribozyme A had shorter annealing arms of 9 nucleotides each, while ribozyme C had arms of 14 (3') and 16 (5') nucleotides.

Antisense control ribozymes, with a G substituted for the A in the conserved GAG sequence in the catalytic unit eliminating catalytic function, were similarly cloned and transcribed. Sense ribozymes were synthesized by transcription from the opposite strand in PGEM3z vector using T7 RNA polymerase.

EXAMPLE 2

Cleavage of Target mRNA With Multi-Unit Ribozyme

A. Cleavage of bcr-abl mRNA.

cDNA encoding a 499 base pair segment of the bcr-abl breakpoint region was cloned into PGEM3 vector (Promega). RNA was transcribed using $^{32}$P-UTP and T7 RNA polymerase, as described above. The resulting $^{32}$p-labelled bcr-abl mRNA containing the breakpoint region was used as a target for single-, double- and triple-unit ribozymes in 2-hour cleavage reactions. Reactions were carried out in 10 µl volumes. All RNA concentrations were 100 nM. RNA was suspended in 50 mM Tris-HCl, pH 7.5, 1 mM EDTA. Samples containing substrate and ribozyme were heated to 95° C. for 5 minutes, then placed on ice. Cleavage reactions were initiated by adding 1 ml of 200 mM MgCl. Reactions were stopped after 2 hours by adding 2 µl of formamide-EDTA dye. Cleavage products were analyzed by electrophoresis on a 6% sequencing gel followed by autoradiography and quantitative densitometry (Fujix, Tokyo, Japan).

Figure 2:
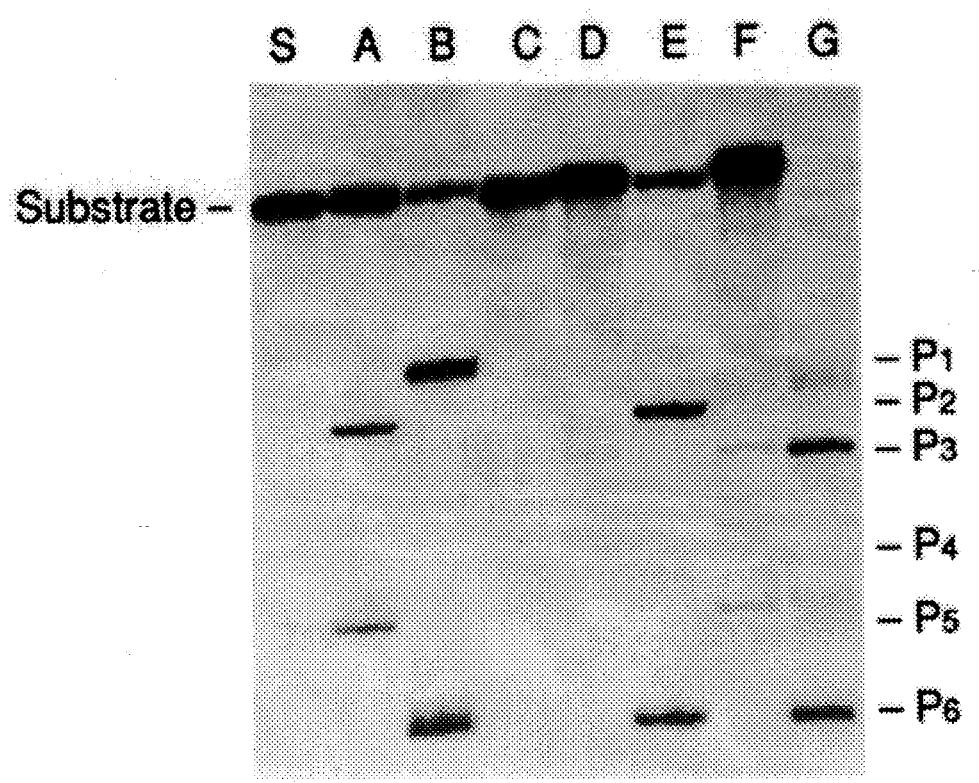
FIG. 2 is an autoradiogram of the ribozyme-mediated cleavage of a target bcr-abl mRNA synthesized from a plasmid vector containing a 499 bp segment of the bcr-abl chimeric gene. Each lane shows the cleavage products resulting from the reaction of single-double-or triple-unit ribozymes targeting sites #1, #2 and/or #3 of the bcr-abl mRNA shown in FIG. 1: Lane A—single-unit ribozyme (SEQ ID NO:7) targeting site #2; lane B—single-unit ribozyme (SEQ ID NO:2) targeting site #1; lane C—single-unit ribozyme (SEQ ID NO:3) targeting site #2; lane D—single-unit ribozyme (SEQ ID NO:4) targeting site #3; lane E—double-unit ribozyme (SEQ ID NO:5) targeting sites #1,2; lane F—double-unit ribozyme (SEQ ID NO:6) targeting sites #2,3; lane G—triple-unit ribozyme (SEQ ID NO:1) targeting sites #1,2,3; and lane S—control containing substrate without ribozymes.

The results are shown in FIG. 2. Lane S represents a control and contains substrate without ribozymes. The ribozymes generating the fragments in Lanes A through G correspond to ribozymes A through G, respectively. Cleavage with double and triple-unit ribozymes released small fragments which ran at the bottom of the gel and are not shown.

As shown in FIG. 2, the ribozymes specifically cleaved bcr-abl mRNA. After 2 hours, single-unit ribozymes cleaved target bcr-abl mRNA into two fragments with variable efficiency. Ribozymes A, B. C and D cleaved 45%, 79%, 5% and 7% of target mRNA, respectively. Comparing ribozymes A and C demonstrates that ribozymes targeting the same site with shorter annealing arms are somewhat more efficient. Double-unit ribozymes E and F cleaved 72% and 13% of target mRNA. There was no significant improvement in cleavage over the best single-unit ribozyme of the pair. However, ribozyme G, the triple-unit ribozyme, cleaved 94% of target mRNA in 2 hours.

There was 0% cleavage of bcr-abl with sense-oriented ribozymes and cleavage-inactive antisense ribozymes (data not shown). In addition, adding all three single-unit ribozymes in one reaction resulted in little additional cleavage compared to the best single ribozyme (data not shown).

B. Cleavage of c-abl and bcr mRNA.

Figure 3A:
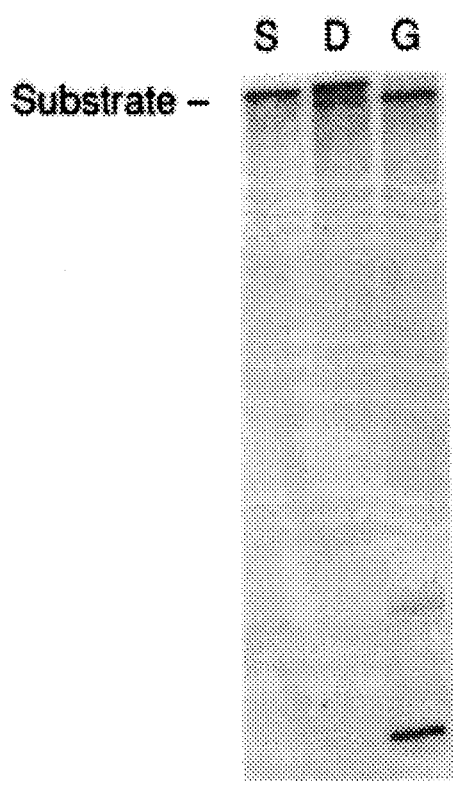
FIGS. 3A and 3B comprise autoradiograms of ribozyme-mediated cleavage of c-abl (FIG. 3A) and bcr (FIG. 3B) mRNA which include the breakpoint region.
Figure 3B:
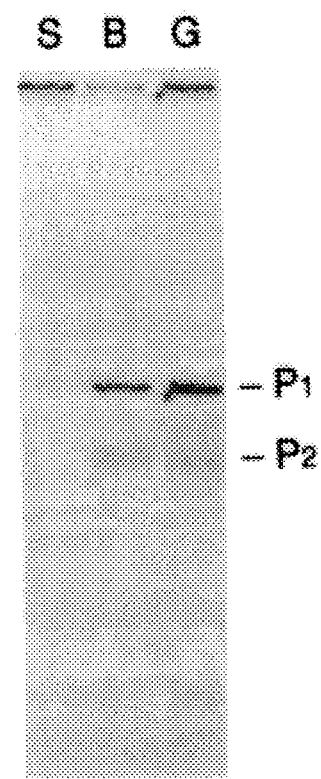

In order to test the specificity of the triple-unit ribozyme, cDNAs encoding a 359 base pair segment of the bcr gene comprising nucleotides 563–873 of the sequence reported by Heisterkamp et al., Nature 315, 758 (1985), and a 447 base pair segment of the abl gene comprising nucleotides −39 to +396, were cloned into PGEM5 and PGEM3z vectors (Promega), respectively. RNA was transcribed using $^{32}$P-UTP and T3 and SP6 RNA polymerases, respectively. The resulting $^{32}$P-labelled c-abl and bcr mRNA containing the breakpoint region was used as a target for single and triple-unit ribozymes in 2-hour cleavage reactions, as above. The results are indicated in FIGS. 3A and 3B, showing specific cleavage products obtained from c-abl (FIG. 3A) and bcr (FIG. 3B) mRNA. FIG. 3A shows the cleavage of c-abl control mRNA (lane S, no ribozymes) in comparison to cleavage by ribozymes D and G. Ribozyme D cleaved 3% and ribozyme G cleaved 21% of c-abl mRNA. FIG. 3B shows the cleavage of bcr control mRNA (lane S, no ribozymes) in comparison to cleavage by ribozymes B and G. Ri-bozyme B cleaved 83% and ribozyme G cleaved 45% of target bcrmRNA. Thus, the more efficient triple-unit bcr-abl. cleaves c-abl and bcr mRNAs, but significantly less effectively than cr-abl mRNA (94% of target cleaved).

EXAMPLE 3 preparation of Folate-polylysine Vector

A. preparation of NHS- or Benzotriazole-Folate.

Folic Acid (Sigma Chemical Co., St. Louis, MO. 1 g, 2.1 mmol) was dissolved in 10 ml of dimethyl sulfoxide (Fluka) pre-dried with a molecular sieve. To this solution, N-hydroxysuccinimide (NHS) (Pierce, 0.242 g., 2 mmol) or N-hydroxybenzotriazole (Fluka, 0.270 g., 2 mmol) was added. At this point 1,3-dicyclohexylcarbodiimide (Fluka, 0.872 g., 4 mmol) dissolved in a small volume of dimethyl sulfoxide was then slowly added to this solution. The reaction was allowed to proceed overnight in the dark at room temperature under stirring. Dicyclohexylurea formed as a white precipitate was removed by filtering twice the reaction mixture through 40 mesh filter paper. The DMSO was then removed by distillation under vacuum at 45° C. until the solution became viscous gel. The product (NHS-folate or benzotriazole-folate) was then crystallized in an excess volume of anhydrous ether. A small amount of methanol was added to accelerate the crystallization process. A fine yellow powder of NHS-folate or benzotriazole-folate formed at this point was subsequently washed twice with anhydrous ether. The product was then dried under vacuum and stored at 4° C.

B. preparation of Folate-Polylysine Complexes.

Polylysine (pLYS$_{90}$, Sigma, 40 mg) was dissolved in 50 mM carbonate/bicarbonate buffer at pH 9.5. A ten-fold molar excess of NHS-folate or benzotriazole-folate dissolved in 500 μl of DMSO was slowly added to the polylysine solution. The pH of the reaction mixture was adjusted to 9, and the reaction was allowed to proceed at room temperature for at least one hour. The reaction mixture was centrifuged and the supernatant was collected. The folate-conjugated polylysine was then separated from free folate by gel-filtering using a PD-10 desalting column (Pharmacia).

C. preparation of Folate-polylysine Vector Containing Ribozyme.

Triple-unit bcr-abl ribozyme (SEQ ID NO:1 ) and folate-polylysine were suspended in 50 μl of a buffer comprising 150 mM NaCl, 20 mM Hepes, pH 7.3 (using RNAse-free water) were mixed gently for 15 minutes. Folate-lysine conjugates of the triple-subunit ribozyme formed spontaneously.

EXAMPLE 4 preparation of Liposome Vector

Lipsosomes containing triple-unit bcr-ab ribozyme (SEQ ID NO:1) were prepared in 100 μl volume as follows. RNA and lipofectin (N-[1-(2,3-diolcyloxy)propyl]-N,N,N-trimethylammonium chloride, "DOTMA") were combined in 100 μl of RNase-free water and gently mixed for 15 minutes. Liposomes containing the triple-subunit ribozyme formed spontaneously.

EXAMPLE 5

Ribozyme Transfection of Cells

A. Transformation of 32D Cells 32D cells, a murine bone marrow stem cell line, was maintained in IMDM with 10% Fetal Bovine Serum (FBS) and 10% WEHI supernatant as a source of murine interleukin-3 (IL-3). A bcr-abl cDNA was transfected into 32D cells by electroporation. Transformed cells were selected for by growth in IL-3-deficient conditions and by neomycin resistance. The presence of the p210$^{bcr-abl}$ tyrosine kinase was confirmed by northern blotting and immunoprecipitation, and autophosphorylation with $^{32}$P-ATP in a kinase assay. Transformed cells were maintained in IMDM with 10% FBS.

B. Multi-unit Ribozyme Transfection of K562 and Transformed 32D Cells.

Transformed 32D cells maintained in IMDM with 10% FBS and cells of the CML cell line K562 maintained in RPMI with 10% FBS were used in the following transfection studies. All cells were washed twice in phosphate-buffered saline (PBS) prior to transfection. In liposome transfection, K562 cells were suspended in reduced serum media (OptimMem 1, Gibco, Gaithersburg, MD) and transformed 32D cells were suspended in serum-free IMDM. Folate-polylysine mediated transfections were carried out in serum-free, folate-free DMEM after K562 and transformed 32D cells were grown in this media with 10% FBS for 3 days. Folate-polylysine and liposome vectors containing ribozyme were prepared as in the preceding Examples. The transfection mix (triple-unit ribozyme in liposome or in folate-polylysine) was added to 4 ml of media containing 1 ×10⁶ K562 of transformed 32D cells.

After 3 hours of ribozyme exposure, total cellular RNA was isolated and was analyzed by electrophoresis on a 6% sequencing gel followed by autoradiography and quantitative densitometry. FIG. 4A shows the improvement in ribozyme uptake in K562 cells using liposome vectors (lane 2) versus naked multi-unit ribozymes (lane 1).

FIGS. 4B and 4C compare 32D cell transfection using 1 g of RNA with increasing quantities of folate-polylysine or lipofectin vector. Using 1 µg of $^{32}$p-labelled ribozyme, cells were transfected with concentrations of lipofectin or folate-polylysine that varied over 4 logs. Ribozyme uptake was greater by folate receptor-mediated transfection. As was demonstrated for liposome vectors, folate-polylysine vectors protected ribozymes from being degraded in serum-free media (data not shown).

EXAMPLE 6

Serial Cell Transfection with Ribozyme Folate-polylysine Vector

To test the availability of the folate receptor for serial transfections, 32D cells were serially transfected with unlabeled and $^{32}$P-labeled ribozymes over 48 hours. Three identical transfections were performed at time zero with either $^{32}$P-labeled (one sample) or unlabeled ribozymes (two samples). After 3 hours, the cells transfected with labeled ribozymes had RNA isolated. Cells transfected with unlabeled ribozymes were supplemented with FBS (10%), IL-3 and 10% WEHI supernatant. After 24 hours, one of the two remaining samples was then washed in PBS and transfected with labeled ribozymes. After 3 additional hours, these cells were washed, had RNA isolated and stored. A second transfection with unlabeled ribozymes was performed on the remaining cells (second dose) and these cells were supplemented as described. After 48 hours, these cells were transfected with labeled ribozymes (third dose) and after 3 hours had RNA isolated as described above. The RNA was analyzed by electrophoresis on a 6% sequencing gel followed by autoradiography and quantitative densitometry. Additional samples were transfected with unlabeled ribozymes and used to maintain cell numbers at 1 ×10⁶ prior to the daily transfection with ribozymes.

Figure 5:
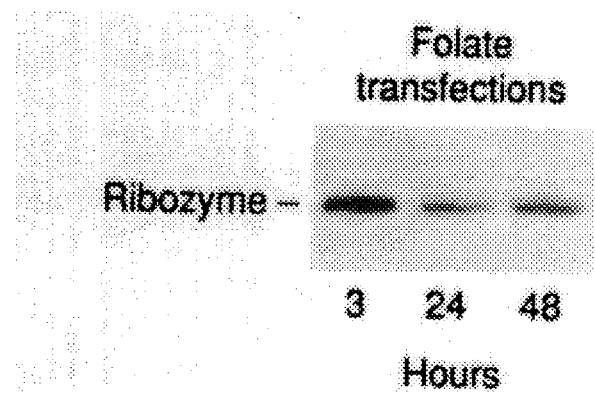
FIG. 5 is an autoradiogram from sequential transfections of triple-unit ribozymes via folate-mediated uptake in 32D cells. Total cellular RNA was isolated 3 hour after transfection. The lanes marked "3", "24" and. "48" represent, respectively, RNA from cells transfected at time zero with $^{32}$P-labeled ribozymes, RNA from cells transfected at time zero with unlabeled ribozymes and at 24 hours with $^{32}$P-labeled ribozymes, and RNA from cells transfected at time zero with unlabeled ribozymes and at 48 hours with $^{32}$P-labeled ribozymes.

The results in FIG. 5 indicate that, compared to the quantity of labeled ribozyme recovered from cells at 3 hours, 50% was recovered after the second transfection and 60% was recovered after the third transfection. Thus, significant quantities of ribozyme continued to be delivered via the folate receptor by serial transfections.

EXAMPLE 7

Analysis of Cellular RNA Following Transfection with Ribozyme

The ability of multi-unit ribozyme to cleave bcr-abl mRNA in cells was determined as follows. Untransformed 32D cells (1 ×10⁶) were added to 1 to 1 ×10⁴ transformed 32D cells and transfected 1–3 times over 24–48 hours with ribozymes via liposomes or folatepolylysine vectors, inactive ribozymes, or transfection media containing no ribozymes. Duplicate transfections were prepared and treated from 1 to 3 times over 24–48 hours. Three hours after transfection, the media was supplemented with FBS and IL-3 as described above. After one or two transfections in 24 hours, or after three transfections in 48 hours, total cellular RNA was extracted by lysing washed cells in Ultraspec™ solution (Biotecx, Houston, Tex.) according to the manufacturer's protocol. Reverse transcription and polymerase chain reaction (RT-PCR) were performed according to Kawasaki et al., *PCR Protocols: A Guide to Methods and Applications*, Academic Press, Inc., New York, N.Y., (1990), p. 21–27, using primers specific for the cr-abl translocation. The primer sequences were GGAGCTGCAG ATGCTGACCA C (SEQ ID NO:9) and TCAGACCCTG AGGCTCAAAG TC (SEQ ID NO:10) The β-actin gene was also amplified as an internal control. Twenty µl of the PCR product was run on 1.5% agarose gel and photographed. Southern blotting was performed as described by Maniatis et al., *Molecular Cloning: A Laboratory Manual*, Cold Spring Harbor Laboratory Press, Cold Spring Harbor, N.Y. (1982), using a probe spanning the bcr-abl junction, GCTGAAGGGC TTTTGAACTC TGCTTA (SEQ ID NO:11).

Figure 6:
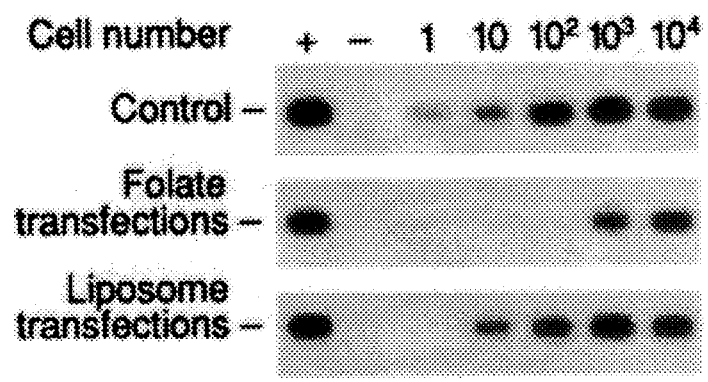
FIG. 6 is an autoradiogram of a Southern blot of RT-PCR-amplified cr-abl mRNA from transformed 32D cells transfected with vectors containing no ribozymes (Control) or triple-unit ribozymes in folate-polylysine (Folate transfections) or liposome vectors (Liposome transfections).

The results are shown in FIG. 6. Transfection with triple-unit ribozyme via folate-polylysine vector resulted in a 3 log decrease in detectable bcr-abl mRNA signal after one transfection in 24 hours. A smaller effect was seen by transfection with ribozymes via liposomes. Cleavage inactive ribozymes had no effect on detection of the bcr-abl mRNA signal (data not shown). RT-PCR using primers that amplified the β-actin gene confirmed that similar quantities of RNA were used in RT-PCR amplification (data not shown).

All references cited with respect to synthetic, preparative and analytical procedures are incorporated herein by reference.

The present invention may be embodied in other specific forms without departing from the spirit or essential attributes thereof and, accordingly, reference should be made to the appended claims, rather than to the foregoing specification, as indication the scope of the invention.

---

We claim:

1. A synthetic RNA molecule which cleaves bcr-abl bcr-abl mRNA comprising
   (a) a first ribozyme subunit comprising
      (i) a first flanking segment having a nucleotide sequence complementary to the nucleotide sequence of a portion of the oncogene mRNA transcript 5' of the oncogene translocation junction and being hybridizable to that mRNA portion;
      (ii) a second flanking segment having a nucleotide sequence complementary to the nucleotide sequence of a portion of the bcr-abl mRNA transcript 3' of the oncogene translocation junction and being hybridizable to that mRNA portion;
      (iii) a catalytically active segment disposed between the first and second flanking segments comprising a ribozyme of the nucleotide sequence SEQ ID NO:8 which cleaves the oncogene mRNA at a G-U-X site comprising nucleotides 6–4 upstream of the oncogene mRNA translocation junction, wherein X is the ribonucleotide A, U, or C;
   (b) a second ribozyme subunit comprising (i) a catalytically active segment comprising a ribozyme of the nucleotide Sequence SEQ ID NO:8 which cleaves the bcr-abl mRNA at a G-U-X site comprising nucleotides 34–32 upstream of the bcr-abl mRNA translocation junction, wherein X is the ribonucleotide A, U, or C, and (ii) flanking segments complementary to the bcr-abl mRNA transcript and hybridizable thereto; and
   (c) a third ribozyme subunit comprising (i) a catalytically active segment comprising a ribozyme of the nucleotide sequence SEQ ID NO:8 which cleaves the bcr-abl mRNA at a G-U-X site comprising nucleotides 18–20 downstream of the bcr-abl mRNA translocation junction, wherein X is the ribonucleotide A, U, or C, and (ii) flanking segments complementary to the bcr-abl mRNA transcript and hybridizable thereto.

2. An RNA molecule according to claim 1 containing one or more restriction enzyme sites for cloning of said molecule or subunit thereof.

3. An RNA molecule according to claim 1 wherein the flanking segments comprise from about 4 to about 24 nucleotides.

4. An RNA molecule according to claim 3 wherein the flanking segments comprise from about 6 to about 12 nucleotides.

5. A recombinant vector comprising DNA which when expressed will provide an RNA molecule according to claim 1.

6. A composition comprising a liposome encapsulating the RNA molecule according to claim 1.

7. A liposome composition according to claim 6 wherein the liposome is formed from a cationic lipid.

8. A liposome composition according to claim 7 wherein the cationic lipid is N-[1-(2,3-[diocyloxy]dioleyloxy)-propyl]-N,N,N-trimethylammonium chloride.

9. A conjugate comprising an RNA molecule according to claim 1 complexed with a cell surface ligand-binding molecule.

10. A conjugate according to claim 9 wherein the cell surface ligand-binding molecule comprises folate.

11. A conjugate according to claim 10 wherein the cell surface ligand-binding molecule is folate-polylysine.

12. A method for inhibiting the proliferation of cells characterized by the presence of the bcr-abl oncogene, which method comprises contacting said cells in vitro with an effective amount of the RNA molecule of claim 1 for a time sufficient to cleave the oncogene mRNA and inhibit the expression of the oncogene.

13. A method according to claim 12 comprising treating bone marrow cells aspirated from a leukemia patient with said synthetic RNA molecule.

14. A method for inhibiting the proliferation of cells characterized by the presence of the bcr-abl oncogene, which method comprises introducing into such cells an artificially-constructed gene which, upon transcription in said cells, produces an RNA molecule according to claim 1.

15. A method according to claim 14 wherein the artificially-constructed gene is introduced into said cells by transfection, by a transducing viral vector or by microinjection.

16. A method for inhibiting the proliferation of cells characterized by the presence of the bcr-abl oncogene, which method comprises treating bone marrow cells aspirated from a leukemia paent by introducing into such cells in vitro an artificially-constructed gene which, upon transcription in said cells, produces an RNA molecule according to claim 1.

17. A method according to claim 16 wherein the artificially-constructed gene is introduced into said cells by transfection, by a transducing viral vector or by microinjection.

18. A synthetic RNA molecule according to claim 1 having the nucleotide sequence SEQ ID NO:1.

19. A method according to claim 12 wherein the synthetic RNA molecule has the nucleotide sequence SEQ ID NO:1.

20. A method according to claim 14 which produces an RNA molecule having the nucleotide sequence SEQ ID NO:1.

21. A method according to claim 16 which produces an RNA molecule having the nucleotide sequence SEQ ID NO:1.

* * * * *

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 156 Nucleotides
( B ) TYPE: nucleic acid (C) STRANDEDNESS: single stranded
(D) TOPOLOGY: linear (xi) SEQUENCE DESCRIPTION: SEQ ID NO:1:

TTCGAAAGUC AGAUGCCUGA UGAGUCCGUG AGGACGAAAC UGGCCGCUGA 50

GACGUCAGGG CUUUUGCUGA UGAGUCCGUG AGGACGAAAC UCUGCUUAAC 100

CTAGGGUGGC UGAGUGCUGA UGAGUCCGUG AGGACGAAAC GAUGACAUUC 150

CTTAAG 156

(2) INFORMATION FOR SEQ ID NO:2:

(i) SEQUENCE CHARACTERISTICS:
        (A) LENGTH: 52 Nucleotides
        (B) TYPE: nucleic acid
        (C) STRANDEDNESS: single stranded
        (D) TOPOLOGY: linear (xi) SEQUENCE DESCRIPTION: SEQ ID NO:2:

GGUGGCUGAG UGCUGAUGAG UCCGUGAGGA CGAAACGAUG ACAUUCCUUA 50

AG 52

(2) INFORMATION FOR SEQ ID NO:3:

(i) SEQUENCE CHARACTERISTICS:
        (A) LENGTH: 53 Nucleotides
        (B) TYPE: nucleic acid
        (C) STRANDEDNESS: single stranded
        (D) TOPOLOGY: linear (xi) SEQUENCE DESCRIPTION: SEQ ID NO:3:

ACGUCAGGGC UUUUGCUGAU GAGUCCGUGA GGACGAAACU CUGCUUAACC 50

TAG 53

(2) INFORMATION FOR SEQ ID NO:4:

(i) SEQUENCE CHARACTERISTICS:
        (A) LENGTH: 51 Nucleotides
        (B) TYPE: nucleic acid
        (C) STRANDEDNESS: single stranded
        (D) TOPOLOGY: linear (xi) SEQUENCE DESCRIPTION: SEQ ID NO:4:

TTCGAAAGUC AGAUGCCUGA UGAGUCCGUG AGGACGAAAC UGGCCGCUGA 50

G 51

(2) INFORMATION FOR SEQ ID NO:5:

(i) SEQUENCE CHARACTERISTICS:
        (A) LENGTH: 105 Nucleotides
        (B) TYPE: nucleic acid
        (C) STRANDEDNESS: single stranded
        (D) TOPOLOGY: linear (xi) SEQUENCE DESCRIPTION: SEQ ID NO:5:

ACGUCAGGGC UUUUGCUGAU GAGUCCGUGA GGACGAAACU CUGCUUAACC 50

TAGGGUGGCU GAGUGCUGAU GAGUCCGUGA GGACGAAACG AUGACAUUCC 100

TTAAG 105

(2) INFORMATION FOR SEQ ID NO:6:

(i) SEQUENCE CHARACTERISTICS:
        (A) LENGTH: 104 Nucleotides (B) TYPE: nucleic acid
(C) STRANDEDNESS: single stranded
(D) TOPOLOGY: linear (xi) SEQUENCE DESCRIPTION: SEQ ID NO:6:

TTCGAAAGUC AGAUGCCUGA UGAGUCCGUG AGGACGAAAC UGGCCGCUGA    50

GACGUCAGGG CUUUUGCUGA UGAGUCCGUG AGGACGAAAC UCUGCUUAAC   100

CTAG   104

(2) INFORMATION FOR SEQ ID NO:7:

(i) SEQUENCE CHARACTERISTICS:
      (A) LENGTH: 41 Nucleotides
      (B) TYPE: nucleic acid
      (C) STRANDEDNESS: single stranded
      (D) TOPOLOGY: linear (xi) SEQUENCE DESCRIPTION: SEQ ID NO:7:

GGGCUUUUGC UGAUGAGUCC GUGAGGACGA AACUCUGCUU A   41

(2) INFORMATION FOR SEQ ID NO:8:

(i) SEQUENCE CHARACTERISTICS:
      (A) LENGTH: 23 Nucleotides
      (B) TYPE: nucleic acid
      (C) STRANDEDNESS: single stranded
      (D) TOPOLOGY: linear (xi) SEQUENCE DESCRIPTION: SEQ ID NO:8:

CUGAUGAGUC CGUGAGGACG AAA   23

(2) INFORMATION FOR SEQ ID NO:9:

(i) SEQUENCE CHARACTERISTICS:
      (A) LENGTH: 21 Nucleotides
      (B) TYPE: nucleic acid
      (C) STRANDEDNESS: single stranded
      (D) TOPOLOGY: linear (xi) SEQUENCE DESCRIPTION: SEQ ID NO:9:

GGAGCTGCAG ATGCTGACCA C   21

(2) INFORMATION FOR SEQ ID NO:10:

(i) SEQUENCE CHARACTERISTICS:
      (A) LENGTH: 22 Nucleotides
      (B) TYPE: nucleic acid
      (C) STRANDEDNESS: single stranded
      (D) TOPOLOGY: linear (xi) SEQUENCE DESCRIPTION: SEQ ID NO:10:

TCAGACCCTG AGGCTCAAAG TC   22

(2) INFORMATION FOR SEQ ID NO:11:

(i) SEQUENCE CHARACTERISTICS:
      (A) LENGTH: 26 Nucleotides
      (B) TYPE: nucleic acid
      (C) STRANDEDNESS: single stranded
      (D) TOPOLOGY: linear (xi) SEQUENCE DESCRIPTION: SEQ ID NO:11:

GCTGAAGGGC TTTTGAACTC TGCTTA   26